United States Patent [19]

Brooks

[11] Patent Number: 4,711,249
[45] Date of Patent: Dec. 8, 1987

[54] CIRCUMFERENTIAL MEMBRANE, FLUID COUPLED CATHETER

[76] Inventor: Albert E. Brooks, 1730 Ocean Oaks, Carpinteria, Calif. 93013

[21] Appl. No.: 889,103

[22] Filed: Jul. 23, 1986

[51] Int. Cl.[4] .............................................. A61B 5/00
[52] U.S. Cl. .................................. 128/748; 128/673; 128/667
[58] Field of Search .............................. 128/664–667, 128/672–673, 675, 748, 642, 715, 772–773; 604/101–103; 73/705, 708, 715

[56] References Cited

U.S. PATENT DOCUMENTS

| | | | |
|---|---|---|---|
| 4,209,023 | 6/1980 | Layton | 128/748 |
| 4,297,890 | 11/1981 | Hok | 128/673 X |
| 4,304,239 | 12/1981 | Perlin | 128/642 |
| 4,346,698 | 8/1982 | Hanson et al. | 604/103 X |
| 4,476,872 | 10/1984 | Perlin | 128/642 |
| 4,517,984 | 5/1985 | Perlin | 128/748 X |
| 4,593,701 | 6/1986 | Kobayashi et al. | 128/673 X |
| 4,595,017 | 6/1986 | Webler et al. | 128/642 |

Primary Examiner—William E. Kamm
Assistant Examiner—Angela D. Sykes
Attorney, Agent, or Firm—Donald D. Mon

[57] ABSTRACT

A medical catheter comprising a tube having an internal lumen with an internal wall in which a rigid insert is fitted between lengths of the tube. The rigid insert is overlapped by the ends of the lengths of the tube and the lengths are spaced apart. The insert has an internal chamber with a port through its wall entering into the spacing between the two ends. A flexible membrane extends entirely around the periphery of the spacing and overlaps the ends of the lengths, thereby closing the spacing and retaining liquid within the spacing and the chamber. The chamber is closed as each end by a respective closure, one of which is flexibly responsive to internal pressure in the chamber.

6 Claims, 4 Drawing Figures

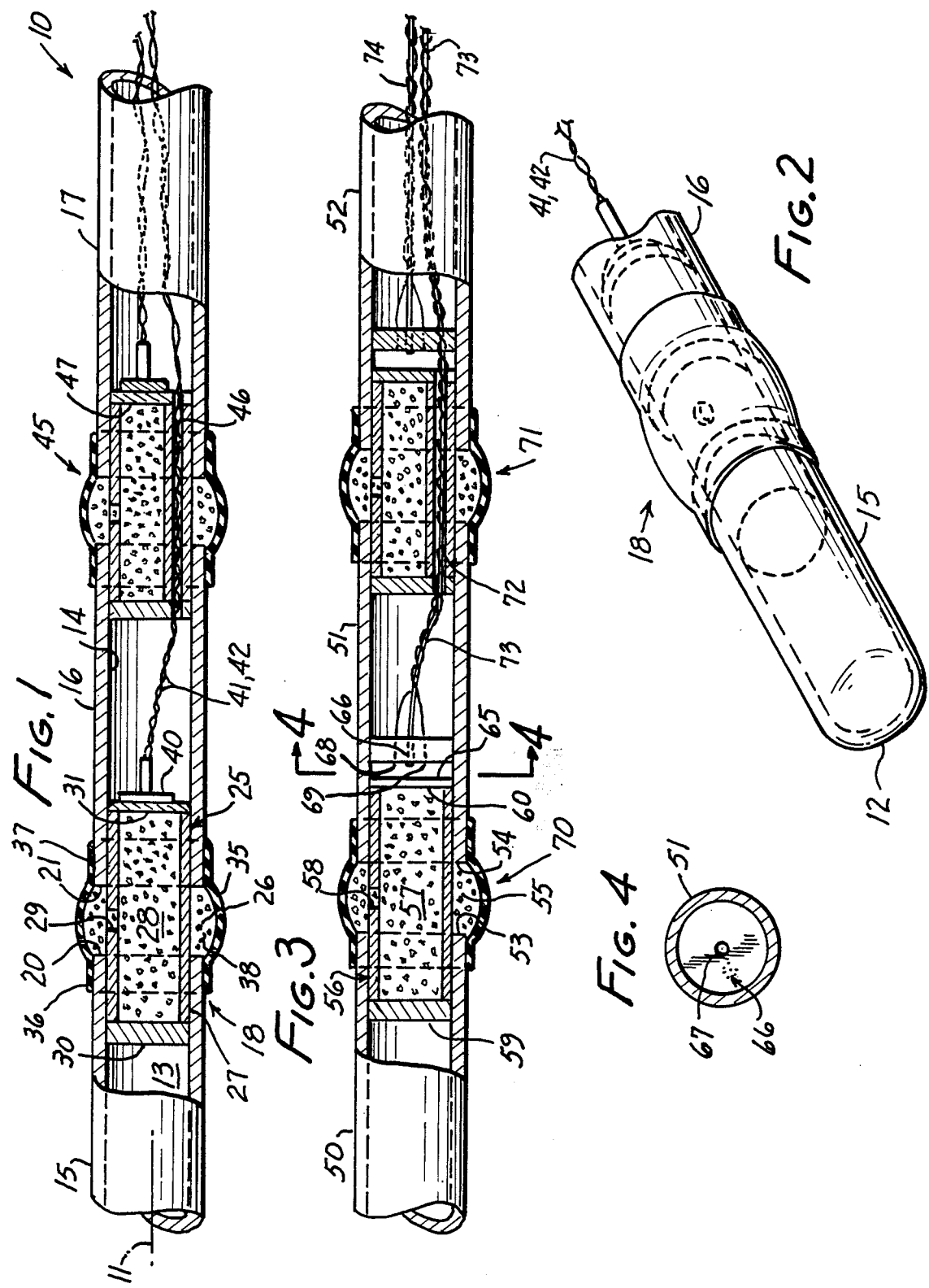

CIRCUMFERENTIAL MEMBRANE, FLUID COUPLED CATHETER

FIELD OF THE INVENTION

This invention relates to medical catheters, and in particular to a catheter which is able to respond to conditions exerted on it around its entire periphery.

BACKGROUND OF THE INVENTION

Pressure, flow rates, and temperatures are parameters that are routinely measured in medical research and clinical procedures. Examples are the measurement of pressure in the bladder, in the urethra, and in the coronary arteries.

Various types of catheters have been devised for these purposes, but in general they can be classified as very delicate, very expensive, subject to substantial errors, or all three. For example, some catheters are fluid filled and measure pressures conveyed by the catheter to the outside of the body. Such catheters are subject to error caused by changes in patient position. Then the fluid column and therefore the readout pressure varies unless the patient is required to remain in one position, which is not always possible or desirable. In addition, the viscosity of the fluid introduces errors which are pressure and temperature related. Even more, because they are temperature sensitive, errors in readings can result because the room temperature can vary during a test. Also because of air conditioning, the room temperature is lower than the body temperature. For this reason, electronic compensation has to be applied.

For these and other reasons other types of catheters have also been developed especially for cardiological procedures where measurements can be very critical.

One improved type of catheter is commercially known as the "Microtip" or miniature strain gage type catheter. These catheters are available in single sensor or multi sensor configurations. They utilize small microchips which are mounted on one side of the catheter body.

The strain gage catheter has major advantages over the use of pressure transducers which convey fluids externally for measuring pressure and flow. This is because the measurement is taken within the body cavity itself. This avoids some of the problems stated above.

However, this type introduces a group of new problems. One is the "rotational effect". In certain body cavities, for example urodynamic pressure measurements in the urethra, tissue pressure can vary significantly from one side of the cavity to the other, making it difficult to measure the genuine overall pressure in the zone being studied. Similarly, arterial pressure measuring can also suffer from the same inaccuracies, depending on the size and location of the vessel.

In addition to the other problems, one of the drawbacks of this class of catheter is its cost and extreme fragility. These cost may hundreds of dollars each and are readily damaged, especially during cleaning, sterilization and patient use.

Optical type sensors have been developed, in which light reflected from a deformable diaphram is sensed to measure the pressure. As to such sensors, their developments have been in the direction of requiring that the sensor be placed at the tip of the catheter. They cannot provide for sensors along the side of the device.

It is an object of this invention to provide a catheter which measures the conditions inside the body without requiring conveying of fluids to the outside of the body, which catheter is rugged, which is not sensitive to location around its periphery, and which can provide for a multiplicity of such sensors along the length of the catheter.

BRIEF DESCRIPTION OF THE INVENTION

A medical catheter according to this invention has a longitudinal axis and includes a longitudinally elongated circularly sectioned support, preferably a tube to be inserted into a body region to be investigated. It has an internal lumen with an internal wall in which a rigid insert is fitted between lengths of the tube. The rigid insert is overlapped by the ends of the lengths of tube and these lengths are thereby spaced apart. The insert has an internal chamber with a port through its wall entering into the spacing between the two ends. A flexible membrane extends entirely around the periphery of the spacing and overlaps the ends of the lengths, thereby closing the spacing and retaining liquid within the spacing and the chamber. The chamber is closed at each end by a respective closure, one of which is flexibly responsive to internal pressure in the chamber.

Sensor means is responsive to flexure of the flexible one of the closures and thereby to the pressure in the chamber. Connector means connected to the sensor means is adapted to connect the sensor means to other means for providing a signal proportional to pressure in the chamber. Should temperature or flow rate be the subject of an investigation, the sensor will be adapted for that purpose.

The above and other features of this invention will be fully understood from the following detailed description and the accompanying drawings, in which:

BRIEF DESCRIPTION OF THE DRAWINGS

FIG. 1 is an axial section of one embodiment of a catheter according to the invention;

FIG. 2 is a perspective view of the tip end of the catheter of FIG. 1;

FIG. 3 is an axial cross-section showing another embodiment of the invention; and FIG. 4 is a cross-section taken at line 4—4 in FIG. 3.

DETAILED DESCRIPTION OF THE INVENTION

In FIG. 1, there is shown a catheter 10 according to the invention. It has a longitudinal axis 11 and a tip end 12 (FIG. 2). Because the catheter must be flexible, it is best made of an elastomeric tubing having a lumen 13 formed with an interior wall 14. The catheter is divided into a plurality of lengths 15, 16, 17 of which three are shown for illustrative purposes. When only one sensing location is used, then the catheter will be divided into only two segments. Because they are all substantially identical, only the left hand sensing element 18 will be described in detail. In this arrangement, lengths 15 and 16 each have respective ends 20, 21 which are spaced apart from one another. The internal wall of the lumen embraces a rigid insert 25. The end portions of the lengths overlap the ends of the rigid insert and may be cemented to it if desired. The ends are spaced apart from one another to leave a spacing 26 between them. The rigid insert has an external cylindrical wall 27 over which the lengths snugly fit. It also has an internal chamber 28. A port 29 interconnects the chamber with the spacing. A first closure 30 closes one end of the chamber. A second closure 31 closes the other. In this embodiment, the first closure is rigid, and the second closure is flexible so it will respond by changing its shape. By changing its shape it will respond to changes in pressure. The change is that of a dome-like structure, preferably symmetrical in all planes that include the axis.

A fully peripheral flexible membrane 35 surrounds the spacing. Its end flanges 36, 37 are cemented to the outside of the respective lengths 15 and 16. The spacing and the chamber are filled with a fluid 38. The fluid might, for example, be normal saline solution which would do no harm to the body should the flexible membrane leak.

Sensor means 40 is attached to the second closure 31. This may be any desired type of strain gauge which is sensitive to the change of configuration of the closure. A plurality of conductive leads 41, 42 are shown connected to the sensor means which extend through the lumen to the outside of the catheter.

Sensor element 45 is identical in all respects to element 18, except that its size and arrangement are modified to provide a passage 46 through which leads 41 and 42 bypass element 45 without going outside of the catheter. The difference in size of the second closure 47 of the element 45 will be modified for this purpose. Except for this, element 45 is identical to element 18 and will not be described in detail further. It will be noted in FIG. 2 that length 15 is closed by a rounded tip end. Also, it will be evident that sufficient fluid is preferably injected into the chambers that there is a slight bowing outwardly of the flexible membrane to provide for more efficient measurement.

The embodiment of FIG. 3 is the presently preferred embodiment of the invention. It differs from the embodiment of FIG. 1 only in the details of its sensor means. As before, there is a plurality of lengths 50, 51, 52 of tubing joined together with ends, such as ends 53, 54 spaced apart by spacing 55. These ends are fitted over and cemented to an insert 56. The insert is rigid and has a chamber 57 connected by port 58 to spacing 55.

The chamber is closed by first closure 59 which is rigid, and by a second closure 60 which is flexible so as to respond to changes in pressure in the chamber.

The second closure has a surface 65 which is reflective to radiant energy usually the energy will be light, and the surface will be silvered. The closure will tend to form a dome when pressure is increased and to return toward a flatter configuration shown when pressure decreases. A source 66 of radiant energy perhaps infrared or luminous energy, is spaced from surface 65, and is focused on it by a lens 67 onto the reflective surface. A plurality of detectors 68, 69 are spaced from and exposed to the second closure in such a way as to detect the energy which will change as a function of the change of curvature of the reflective surface, thereby to provide an output which can be converted into a signal useful for measurement purposes. Two elements 70, 71 which differ only in size, as in the situation of FIG. 1, enable a passage 72 to be provided which will pass leads 73 from element 70 and join with leads 74 going to the access end of the catheter.

The fluid in the chamber and in the spacing may be thought of as "encapsulated" in an enclosure which is exposed to pressures to which the peripheral membrane is exposed, and with a flexible closure which elastically responds to those pressures all the way around the catheter. Thus, the surrounding pressure is transmitted by the fluid to the flexible closure, which in turn provides sensor means for pressure readout purposes.

It will now be seen that the pressure and temperature measurements can be made fully peripherally and that contact with the wall of the artery or other structure being investigated will not effect the total measurement. The device is simple in construction, and the inserts can be made short enought that they do not appreciably change the flexibility of the catheter to such an extent as to make it inconvenient or impossible to use.

Conventional readout means are provided to receive and process the signals derived from the sensors. These are well-known and are completely conventional.

The device is simple in concept and construction and can readily be manufactured and repaired. In fact, it is sufficiently inexpensive that it may be considered a throwaway article instead of requiring repair. The materials of construction are those which are acceptable for use in the human body, for example silicone rubber for the tubing and for the membranes, and saline solution for the fluid. Only one element need be provided, although any desired number could be provided as shown, depending on the investigation being made. The insert and the first closure may be made of stainless steel. The first closure may be integral with the tubular part of the insert. The flexible closure may be a thin stainless steel diaphram, or may be made of silicone rubber.

This invention is not to be limited by the embodiments shown in the drawings and described in the description which are given by way of example and not of limitation, but only in accordance with the scope of the appended claims.

I claim:

1. A fully circumferentially responsive medical catheter having a longitudinal axis, and comprising:

a longitudinally elongated circularly sectioned support tube for insertion into a body region to be investigted, said support tube having an internal lumen with an internal wall, and being divided into a plurality of lengths, each length having an end;

a rigid insert inserted into the lumen of two adjacent lengths, making a sealing fit therewith, portions of said lengths overlapping said insert with their ends spaced apart from one another to leave a spacing between them, said insert having a cylindrical outer wall and an internal chamber, there being a port through said wall interconnecting said chamber and closing said spacing, and a closure at each end of said chamber closing the same, one closure being rigid and the other closure being elastically flexible to respond to pressure changes in the chamber;

a flexible membrane extending entirely around said spacing and overlapping said ends of said lengths, whereby to close said spacing, leaving the spacing as a continuous peripheral cavity and retain a liquid within said spacing and chamber, said spacing and chamber thereby containing said liquid as an encapsulation inside said membrane; insert and closures;

sensor means responsive to flexure of the flexible closure and thereby to pressure in said chamber; and connector means connected to said sensor means adapted to connect the sensor means to means for providing a signal proportional to pressure in said chamber.

2. A catheter according to claim 1 in which said sensor means is a strain gauge bonded to said flexible closure.

3. A catheter according to claim 1 in which said sensor means comprises a source of radiant energy and a detector of radiant energy, said flexible closure being reflective of said radiant energy and so disposed and arranged as to assume different curvatures for different chamber pressures.

4. Apparatus according to claim 1 in which at least three said lengths are provided, and in which one of said inserts is provided between respective pairs of ends as described, there being sensor means and connector means respective to each of said inserts, and in which at least one of said inserts includes an axial passage to pass the connector means from the other said insert.

5. A catheter according to claim 4 in which said sensor means is a strain gauge bonded to each said flexible closure.

6. A catheter according to claim 4 in which said sensor means each comprises a source of radiant energy and a detector of radiant energy, said flexible closure being reflective of said radiant energy and so disposed and arranged as to assume different curvatures for different chamber pressures.

* * * * *